United States Patent [19]

Brown

[11] Patent Number: 5,159,116

[45] Date of Patent: Oct. 27, 1992

[54] CHEMICALLY AND OPTICALLY PURE B-HALODIISO-2-ETHYLAPOPINOCAMPHEYLBORANES

[75] Inventor: Herbert C. Brown, West Lafayette, Ind.

[73] Assignee: Aldrich Chemical Company, Inc., Milwaukee, Wis.

[21] Appl. No.: 729,610

[22] Filed: Jul. 15, 1991

[51] Int. Cl.$^5$ ............................................. C07F 5/02
[52] U.S. Cl. ................................................ 568/1
[58] Field of Search ........................................... 568/1

[56] References Cited

U.S. PATENT DOCUMENTS 4,772,752 9/1988 Brown ........................................ 568/1

OTHER PUBLICATIONS

Jadhav et al., "Chiral Synthesis via Organoboranes.", *J. Org. Chem.*, 1986, vol. 51, pp. 432–439.

Brown et al., "Selective Reductions.", *J. Org. Chem.*, 1989, vol. 54, pp. 4505–4511.

*Primary Examiner*—Marianne M. Cintins
*Assistant Examiner*—Margaret J. Argo
*Attorney, Agent, or Firm*—Niblack & Niblack

[57] ABSTRACT

A chemically and optically pure B-halodiiso-2-ethylapopinocampheylborane of essentially 100% ee represented by the formula:

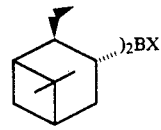

wherein B is borane and X is halo.

9 Claims, No Drawings

CHEMICALLY AND OPTICALLY PURE B-HALODIISO-2-ETHYLAPOPINOCAMPHEYL-BORANES

BACKGROUND OF THE INVENTION

Asymmetric reduction of prochiral ketones produces optically active alcohols. In view of the importance of such reductions, considerable effort has been expended in finding asymmetric reducing agents which will achieve reduction of such carbonyl groups to give optically active alcohols of high optical purity.

The first successful preparation of an efficient chiral organoborane reducing agent was achieved by Professor Mark Midland (See Midland, M. M.; Tramontano, A.; Zderic, S. A. *J. Am. Chem. Soc.* 1979, 101, 2352) who synthesized B-isopinocampheyl-9-borabicyclo[3.3.1]nonane (sold by Aldrich Chemical Company, Inc., Milwaukee, Wis. under the trademark Alpine-Borane ®). This reagent is very efficient in reducing reactive carbonyl groups such as α-deuteraldehydes, α,β-acetylenic ketones, α-keto esters and α-halo ketones. However, chiral reduction of slower reacting ketones such as aralkyl and dialkyl ketones were not successful.

To overcome these deficiencies, B-chlorodiisopinocampheylborane (Ipc$_2$BCl) (sold by Aldrich Chemical Company, Inc., Milwaukee, Wis. under the trademark DIP-Chloride ®) was developed. B-chlorodiisopinocampheylborane reacts with ketones at a considerably faster rate than the Alpine-Borane reagent (Brown, H. C.; Chandrasekharan, J; Ramachandran, P. V. J., *J. Am. Chem. Soc.* 1988, 110, 1539). Ipc$_2$BCl is an excellent reagent for the reduction of prochiral aralkyl ketones and provides essentially optically pure product alcohols for most types of aralkyl ketones. It is also highly effective for reducing α-quaternary alkyl ketones. The success of reduction of such ketones with Ipc$_2$BCl may be explained by a tentative mechanism where the α-quaternary alkyl group has to sterically interact with the methyl group at the 2-position of the isopinocampheyl moiety. However, when the steric interaction between the reagent and the ketone is less as is the case of the reduction of 3-methyl-2-butanone (32% ee) and 2-butanone (4% ee), the chiral induction is poor.

It remains highly desirable to develop a reagent which will reduce a broad spectrum of ketones. The present invention provides B-halodiiso-2-ethylapopinocampheylboranes which fulfill that need.

One of the compounds of this invention was reported by Jadhav., P. K.; Bhat, K. S.; Perumal, P. T.; Brown, H. C., *J. Org. Chem.* 1986, 51, 432, bis(10-methylisopinocampheyl)chloroborane. The compound was only of 92% ee and 92% chemical purity which is not sufficient for use in chiral reductions. The compounds of this invention are chemically and optically pure.

SUMMARY OF THE INVENTION

The present invention provides novel chemically and optically pure (−) and (+)-B-halodiiso-2-ethylapopinocampheylboranes represented by the formula:

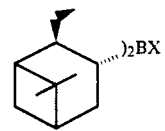

wherein X is halo.

The term "halo", as used herein, refers to chloro, bromo, fluoro and iodo.

For convenience, the compounds of this invention may also be represented by the formula:

Eap$_2$BX wherein X is halo.

The compounds of this invention may also be represented by the formulae:

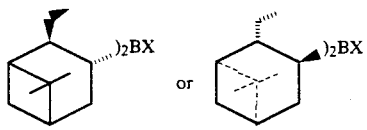

The compounds of this invention include:
(−)-B-Chlorodiiso-2-ethylapopinocampheylborane;
(+)-B-Chlorodiiso-2-ethylapopinocampheylborane;
(−)-B-Bromodiiso-2-ethylapopinocampheylborane;
(+)-B-Bromodiiso-2-ethylapopinocampheylborane;
(−)-B-Iododiiso-2-ethylapopinocampheylborane;
(+)-B-Iododiiso-2-ethylapopinocampheylborane;
(−)-B-Fluorodiiso-2-ethylapopinocampheylborane;
(+)-B-Fluorodiiso-2-ethylapopinocampheylborane;

The preferred compounds are those wherein X is chloro or bromo.

The compounds of this invention are useful as reducing agents in the asymmetric reduction of ketones to optically active alcohols of high optical purity. They are useful in reducing those ketones for which the commercially available agent, B-chlorodiisopinocampheylborane is very effective, and in addition, are useful for reducing all those ketones with an α-sec-alkyl group adjacent to the carbonyl moiety to produce alcohols in essentially optically pure form (essentially 100% ee).

The term "essentially 100% ee", as used herein, refers to an enantiomeric excess of at least 95% of one of the members of an enantiomeric pair. The term "optically pure" is synonymous.

The term "ee" is an abbreviation for enantiomeric excess.

The term "enantiomeric pair" refers to a pair of substances whose molecules are nonidentical mirror images.

The optically active boron halides of the present invention are optically stable over reasonable periods of time. Moreover, they are exceptionally reactive reducing agents, reacting far faster with carbonyl compounds than B-isopinocampheyl-9-borabicyclo[3.3.1]nonane. On reaction with prochiral α-secondary alkyl ketones, they produce product alcohols of much higher ee than those provided by B-chlorodiisopinocampheylborane.

Generally speaking, the boron halides of this invention may be conveniently prepared by treating (+) or (−)-2-ethylapopinene with a haloborane-methylsulfide complex represented by the formula BH$_2$X.SMe$_2$. The process is represented by the following reaction scheme:

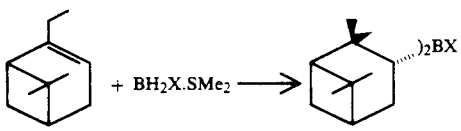

It is preferred to dissolve the (+) or (−)-2-ethylapopinene in a suitable solvent such as, for example, ethyl ether, pentane, tetrahydrofuran, and dichloromethane in the cold prior to addition of the haloborane-methylsulfide complex. The reaction mixture may then be warmed to room temperature where it is maintained at ambient temperature for a period of from 24 h to 36 h until completion. Solvents are then removed by conventional procedures.

The reaction is simple, straight-forward and produces the compounds of this invention in essentially 100% ee. Alternatively, (+)- or (−)-2-ethylapopinene may be treated with $H_2BX$ when X is bromo or chloro to obtain the compounds of this invention. When X is fluoro or iodo, the compounds may be conveniently prepared by treating (+)- or (−)-$Eap_2BH$ with $H_2F$ or $\frac{1}{2} I_2$.

The following examples further illustrate the present invention. All operations were carried out under nitrogen.

EXAMPLE 1

Preparation of (+)-B-Chlorodiiso-2-ethylapopinocampheylborane

An oven-dried 250 mL round-bottom flask equipped with a side-arm capped with a rubber septum, a magnetic stirring bar and a connecting tube attached to a mercury bubbler was flushed with nitrogen. The flask was immersed in an ice bath and 30 g (200 mmol) of (−)-2-ethylapopinene $[\alpha]D^{24} = -46.4°$ (99% ee) was dissolved in 60 mL of freshly distilled (over $P_2O_5$) dichloromethane. The solution was cooled at ice bath temperature for 15 min and $BH_2Cl.SMe_2$ (Aldrich Chemical Company, Milwaukee, Wis.)(10.9 mL of 9.2M, 100 mmol) was added dropwise. The reaction mixture was allowed to warm to room temperature and was left at that temperature for 36 h. $^{11}B$ NMR spectrum showed a major peak at $\delta$ 74 ppm corresponding to the required reagent $Eap_2BCl$ and a minor peak at $\delta$ 11 ppm. Solvents were removed at aspirator vacuum. The residue was dissolved in dry pentane when a small amount of a white precipitate was observed. The supernatant was decanted into another 100 mL flask. $^{11}B$ NMR spectrum of an aliquot at this stage showed a composition of >98% $Eap_2BCl$ ($\delta$ 74 ppm) and <2% of an impurity at $\delta$ 18 ppm, probably corresponding to $EapBCl_2.SMe_2$. Methanolysis of the aliquot showed corresponding amounts of iso-2-ethylapopinocampheylborinate and iso-2-ethylapopinocampheylboronate ($^{11}B$ NMR spectrum: $\delta$ 52 ppm and 32 ppm), respectively. The yield of $Eap_2BCl$ is 95%.

EXAMPLE 2

Preparation of (−)-B-Chlorodiiso-2-ethylapopinocampheylborane

Following the method of example 1, the title compound was prepared from (+)-2-ethylapopinene and chloroboranemethylsulfide complex.

EXAMPLE 3

Preparation of (+)-B-Bromodiiso-2-ethylapopinocampheylborane

The title compound was prepared from (−)-2-ethylapopinene and bromoborane-methylsulfide complex following the method of example 1.

EXAMPLE 4

Preparation of (−)-B-Bromodiiso-2-ethylapopinocampheylborane

The title compound was prepared from (+)-2-ethylapopinene and bromoborane-methylsulfide complex following the method of example 1.

EXAMPLE 5

Reduction of 3-methyl-2-butanone with $Eap_2BCl$

An oven dried 100 mL round-bottom flask equipped with a septum-capped side arm, magnetic stirring bar and stopcock adaptor connected to a mercury bubbler was assembled while hot and flushed with a stream of nitrogen. (+)-B-Chlorodiiso-2-ethylapopinocampheylborane ($Eap_2BCl$)(9.6 g, 27.5 mmol) was transferred into the flask using a syringe. Ethyl ether (20 mL) was added and the flask was cooled to $-25°$ C. and 3-methyl-2-butanone (2.68 mL, 25 mmol) was added dropwise and stirring continued. Aliquots were methanolyzed at the reaction temperature at periodic intervals and the reaction was monitored by $^{11}B$ NMR spectroscopy. On completion of the reaction (48 h) the mixture was warmed to room temperature and diethanolamine (2.2 equiv) was added when the boron components precipitated out. Stirring was continued for 2 h and the precipitate was filtered off and washed with pentane. Solvents were removed by distillation and the alcohol was collected at 110°-112° C. Yield: 1.32 g (60%). The menthylchloroformate derivative of the alcohol was made as usual and analysis on a SPB-5 (30 m) capillary column showed 95% ee in the R-isomer of the alcohol.

Further distillation provided 1.7 g (45%) of 2-ethylapopinene. The recovered 2-ethylapopinene showed physical properties identical to the starting material.

As an alternative work up procedure, acetaldehyde was added to the reaction mixture after completion of the reduction and let stand overnight. $^{11}B$ NMR spectrum showed a singlet at approximately $\delta$ 18 ppm. Aqueous NaOH was added at this stage and the organics extracted with ether and concentrated to provide the alcohol in 80% yield. 2-Ethylapopinene was recovered in 90%. The physical properties of the recovered 2-ethylapopinene were identical to the starting material.

EXAMPLE 6

Reduction of acetophenone with $Eap_2BCl$

Following the set-up of Example 5 and under a nitrogen atmosphere, acetophenone (2.9 g, 3.0 mL, 25 mmol) was added to a solution of B-chlorodiiso-2-ethylapopinocampheylborane (9.6 g, 27.5 mmol) in EE (ethyl ether, 20 mL) at $-25°$ C. The reaction was complete in 48 h (followed by $^{11}B$ NMR after methanolysis of an aliquot). The reaction was worked up following the procedure of Example 3 to obtain 2.2 g, 72% of α-phenethyl alcohol which was found to be of $\geq 99\%$ ee by capillary GC analysis of its MTPA ester.

EXAMPLE 7

Reduction of acetylcyclohexane with Eap₂BCl

Following the method of Example 6, acetylcyclohexane (3.15 g, 25 mmol) was added to a solution of B-chlorodiiso-2-ethylapopinocampheylborane (9.6 g, 27.5 mmol) in EE (20 mL) at −25° C. The reaction was complete in 48 h (followed by $^{11}$B NMR after methanolysis of an aliquot). The reaction was worked up as in Example 5 to obtain 2.24 g, 70% of 1-cyclohexylethanol (97% ee as determined by capillary GC analysis of its MTPA ester).

EXAMPLE 8

Reduction of methylcyclohexanone with Eap₂BCl

Under a nitrogen atmosphere, with the usual set up, a solution of B-chlorodiiso-2-ethylapopinocampheyl (8.7 g, 25 mmol) in EE (20 mL) at −25° C. was added to a solution of 2-methylcyclohexanone (5.6 g, 50 mmol) in EE (20 mL) at −25° C. The reaction was complete in 3 h (followed by $^{11}$B NMR after methanolysis of an aliquot). The solvents were removed in aspirator vacuum and the residue was subjected to high vacuum (0.01 Torr) when the liberated 2-ethylapopinene and excess ketone were collected in the trap cooled with a dry ice-acetone bath. The residue was worked up as in Example 3 to obtain 2.2 g, 72% of trans-2-methylcyclohexanol which was found to be of ≧99% isomeric purity and ≧99% ee by capillary GC analysis of its MTPA ester.

EXAMPLES 9–16

The chiral reduction of representative ketones with Eap₂BCl in EE at −25° C. was carried out and the results summarized in Table 1. Literature values of the commercial prior art reagent Ipc₂BCl are given for comparison.

TABLE 1

Asymmetric Reduction of Representative Ketones with (+)-Eap₂BCl at −25° C.

| Ketone | Reaction time | Yield, % | % ee (+)Eap₂BCl | % ee Ipc₂BCl |
|---|---|---|---|---|
| 3-methyl-2-butanone | 48 h | 60 | 95(R) | 32 |
| acetylcyclohexane | 48 h | 70 | 97(R) | 26 |
| 2,2-dimethylcyclopentanone | 24 h | 71 | ≧99(R)[a] | 98 |
| acetophenone | 48 h | 72 | ≧99(R) | 98 |
| 3-acetylpyridine | 10 d | 70 | ≧99(R) | 92 |
| 2-chloroacetophenone | 7 d | 73 | ≧99(S)[b] | 95 |
| methyl benzoylformate | 1 h | 85 | 70(S)[b] | 50 |
| trans-4-phenyl-3-buten-2-one | 14 d | 60 | 81(R) | 81 |
| 2-cyclohexenone | 7 d | 60 | 74(R) | 36 |
| 4-phenyl-3-butyn-2-one | 3 h | 82 | 33(S)[b] | 21 |

[a]Room temperature reaction. [b]Opposite configuration is an artifact of Cahn-Ingold-Prelog rules.

EXAMPLES 17–26

Table 2 compares results achieved with Eap₂BCl and six commonly used reagents for the asymmetric reduction of nine representative ketones (aliphatic, alicyclic, aralkyl, heteroaralkyl, α-haloketones, olefinic, conjugated olefinic, α-keto esters, β-keto esters and α,β-acetylenic ketones) as follows: 1=3-methyl-2-butanone; 2=2,2-dimethylcyclopentanone; 3=acetophenone; 4=3-acetylpyridine; 5=2-chloroacetophenone; 6=methyl benzoylformate; 7=trans-4-phenyl-3-buten-2-one; 8=2-cyclohexen-1-one; 9=4-phenyl-3-butyn-2-one.

TABLE 2

ASYMMETRIC REDUCTION OF REPRESENTATIVE KETONES

% ee

| Ketone | Alpine Borane | Ipc₂BCl | Itsuno's Reagent | NB-Enantride | K-Glucoride | Binal-H | Eap₂BCl |
|---|---|---|---|---|---|---|---|
| 1 | 62 | 32 | 60 | 68+ | 36 | 78+ | 95++ |
| 2 | 20 | 98++ | 96+ | 1 | 84+ | 11 | ≧99++ |
| 3 | 87 | 98++ | 94+ | 70 | 78 | 95+ | ≧99++ |
| 4 | 93+ | 92+ | 73 | 8 | 70 | — | ≧99++ |
| 5 | 96+ | 95+ | 96+ | 41 | 7 | 95+ | ≧99++ |
| 6 | 90+ | 50 | 25 | 33 | 92++ | 24 | 70 |
| 7 | 56 | 81++ | 6 | 13 | 60 | 70+ | 81++ |
| 8 | 30 | 36 | 35 | — | — | — | 74++ |
| 9 | 83+ | 21 | 7 | 10 | 61 | 89++ | 33 |

+ denotes good reagent and ++ denotes excellent reagent as compared to other reagents currently available.

EXAMPLE 27

Preparation of (−)-B-Bromodiiso-2-ethylapopinocampheylborane

The title compound was prepared following the method of Example 1 using H₂BBr and (−)-2-ethylapopinene.

EXAMPLE 28

Preparation of (+)-B-Bromodiiso-2-ethylapopinocampheylborane

The title compound was prepared following the method of Example 1 using H₂BBr and (+)-2-ethylapopinene.

EXAMPLE 29

Preparation of (−)-B-Iododiiso-2-ethylapopinocampheylborane

The title compound is prepared by treating (−)-diiso-2-ethylapopinocampheylborane (Eap₂BH) with I₂.

EXAMPLE 30

Preparation of
(+)-B-Iododiiso-2-ethylapopinocampheylborane

The title compound was prepared following the method of Example 29 using I$_2$ and (+)-diiso-2-ethylapopinocampheyl borane.

EXAMPLE 31

Preparation of
(−)-B-Fluorodiiso-2-ethylapopinocampheylborane

The title compound was prepared following the method of Example 29 using HF in place of I$_2$.

EXAMPLE 32

Preparation of
(+)-B-Fluorodiiso-2-ethylapopinocampheylborane

The title compound was prepared following the method of Example 30 using HF in place of I$_2$.

EXAMPLE 33

Preparation of
(+)-B-Bromodiiso-2-ethylapopinocampheylborane

Following the method of example 1, the title compound was prepared from (−)-ethylapopinene and bromoboranemethylsulfide complex.

EXAMPLE 34

Preparation of
(−)-B-Bromodiiso-2-ethylapopinocampheylborane

The title compound was prepared from (+)-ethylapopinene and bromoborane-methylsulfide complex following the method of example 1.

EXAMPLE 35

Reduction of 3-methyl-2-butanone with Eap$_2$BBr

An oven dried 100 mL round-bottom flask equipped with a septum-capped side arm, magnetic stirring bar and stopcock adaptor connected to a mercury bubbler was assembled while hot and flushed with a stream of nitrogen. B-Bromodiiso-2-ethylapopinocampheylborane (Eap$_2$BBr)(9.6 g, 27.5 mmol) was transferred into the flask using a syringe. Dichloromethane (20 mL) was added and the flask was cooled to −25° C. and 3-methyl-2-butanone (2.68 mL, 25 mmol) was added dropwise and stirring continued. Aliquots were methanolyzed at the reaction temperature at periodic intervals and the reaction was monitored by $^{11}$B NMR spectroscopy. On completion of the reaction (48 h) the mixture was warmed to room temperature. Dichloromethane was substituted with ethyl ether and diethanolamine (2.2 equiv) was added when the boron components precipitated out. Stirring was continued for 2 h and the precipitate was filtered off and washed with pentane. Solvents were removed by distillation and the alcohol was collected at 110°–12° C.

EXAMPLE 36

Reduction of acetophenone with Eap$_2$BBr

Following method of Example 5, acetophenone is reduced using B-bromodiiso-2-ethylapopinocampheylborane in place of B-chorodiiso-2-ethylapopinocampheylborane with similar results.

EXAMPLE 37

Reduction of acetylcyclohexane with Eap$_2$BBr

Following the method of Example 6, acetylcyclohexane is reduced using B-bromodiiso-2-ethylapopinocampheylborane with similar results.

EXAMPLE 38

Reduction of methylcyclohexanone with Eap$_2$BI

B-iododiiso-2-ethylapopinocampheylborane is substituted for Eap$_2$BCl in the procedure of Example 8 with similar results.

EXAMPLE 39

Reduction of methylcyclohexanone with Eap$_2$BF

B-fluorodiiso-2-ethylapopinocampheylborane is substituted for Eap$_2$BCl in the procedure of Example 8 with similar results.

EXAMPLE 40

Preparation of (−)-2-Ethylapopinene

A dry, 2-L flask equipped with a septum inlet, magnetic stirring bar, and a reflux condenser leading to a mercury bubbler was flushed with dry nitrogen and maintained under static pressure of nitrogen. The flask was charged with 170 mL (1 mol) of (−)-nopol [[α]$^{23}$D 40.2 (neat)] and 400 mL tetrahydrofuran (THF) and cooled to −78° C. While the solution was stirring at −78° C., 455 mL (2.2M, 1 mol) of n-BuLi was added slowly and stirred for 1 h at −78° C.; 190 g (1 mol) of p-toluenesulfonyl chloride in 200 mL of THF was added slowly and the stirring continued for another hour at at −78° C. It was then warmed to room temperature and stirred for 2 h. The reaction mixture was poured into ice-water and extracted with pentane. Evaporation of the solvent gave a thick semi-solid of nopol tosylate in 90% yield (290 g). Nopol tosylate (290 g) was dissolved in hot pentane (800 mL) and stored at 0° C. for 12 h to insure complete crystallization. Colorless white needles of Nopol tosylate (mp 50°–51° C.) were recovered by fast filtration in 85% yield.

A dry, 3-L flask was charged with 31 g (0.77 mol) of lithium aluminum hydride (LAH) and 1500 mL of anhydrous ether. The tosyl derivative prepared above (234 g, 0.77 mol in ether, 250 mL) was added slowly at 25° C. and refluxed for 5 h. The reaction mixture was poured into ice-water slowly with stirring. The solid Al(OH)$_3$ was filtered off and the filtrate saturated with NaCl and extracted with ether (3×150 mL). The combined organic layer was washed with dilute HCl and brine. The crude oil obtained after the evaporation of solvent was distilled from a small excess of LAH to afford pure (−)-2-ethylapopinene in 61% overall yield, [α]$^{23}$D 46.4 (neat), bp 88° C./40 mm.

EXAMPLE 41

Preparation of (+)-2-Ethylapopinene t-BuOK (76.3 g, 0.68 mole) was placed in a dry 1-L flask equipped with a magnetic stirring bar, septum inlet, and an adapter for nitrogen and cooled to −78° C. To it was added hexane (250 mL), (+)-α-pinene [α]$_{23}$D+51.45° (neat), 99.7% ee; 68 g (0.5 mol), followed by n-BuLi (2.5M, 272 mL, 0.680 mole). The reaction mixture was slowly allowed to warm to room temperature and stirring continued for 48 h. The resulting potassium salt was dissolved in THF (200 mL) and cooled to −78° C. Methyl iodide (142 g, 1 mole) was added slowly to the above solution (30 min). Stirring was continued at −78° C. for 1 h and the mixture was warmed to room temperature and stirred for 1 h. It was then poured onto 1 L of water. The organic layer was separated and the aqueous layer was saturated with potassium carbonate and extracted with hexane (2×50 mL). The combined organic layer was washed with water and brine, dried and evaporated. Distillation of the residue gave an oil (70 g, 83% yield) consisting mainly of (+)-2-ethylapopinene (92%) along with ~2% α-pinene and 6% of an isomeric product, which was fractionated on a packed (Helipack) column (height 1 m, reflux ratio 50:1). The fraction boiling at 70° C./40 mm (7 mL) consisting mainly of α-pinene was discarded. The residue (61 g) containing (+)-2-ethylapopinene (92%) and the isomeric product was stirred over 9-BBN (4.8 g, 10 mol %) at room temperature for 4 h. Distillation afforded (+)-2-ethylapopinene in 65% yield (54 g) GC purity 98%. A small portion of the sample was further purified by preparative GC to obtain 100% GC pure product $[\alpha]^{23}D$ +46.4° (neat, d=0.864), 99.7% ee.

EXAMPLE 42

Preparation of Bis Adduct of Mono(2-ethylapaisopinocampheyl)borane with TMED (Eap$_2$BH)

A dry 500 mL round-bottom flask equipped with septum inlet, magnetic stirring bar and reflux condenser leading to a mercury bubbler was flushed with dry nitrogen and maintained under a static pressure of nitrogen. The flask was charged with 10 mL (10M, 100 mmol) of neat borane-methylsulfide complex and 55 mL of anhydrous ether; 36 mL (210 mmol) of (−)-2-ethylapopinene $[[\alpha]^{23}D$ −42° (neat)] was added dropwise with stirring. The reaction mixture was heated under reflux (4 h) until no BH$_3$ was observed ($^{11}$B NMR). TMED (7.5 mL, 50 mmole) was added to the refluxing solution and the refluxing was continued for another 0.5 h. The product crystallized. Methyl sulfide and 2-ethylapopinene were removed by filtration, and the solid was washed with cold ether (2×10 mL) and dried under vacuum; yield 18.0 g (77%). The white solid was recrystallized (2:1 cyclohexane/toluene); mp 138°–141° C. 2-Ethylapopine $[\alpha]D^{23}$=46.4° (99.7% ee) liberated from this intermediate is used to make the compound of Example 1.

We claim:

1. A chemically and optically pure (+)- or (−)-B-halodiiso-2-ethylapopinocampheylborane of essentially 100% ee represented by the formula:

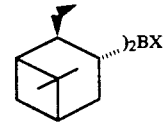

wherein B is borane and X is halo.

2. A compound of claim 1, (−)-B-chlorodiiso-2-ethylapopinocampheylborane.

3. A compound of claim 1, (+)-B-chlorodiiso-2-ethylapopinocampheylborane.

4. A compound of claim 1, (−)-B-bromodiiso-2-ethylapopinocampheylborane.

5. A compound of claim 1, (+)-B-bromodiiso-2-ethylapopinocampheylborane.

6. A compound of claim 1, (−)-B-iododiiso-2-ethylapopinocampheylborane.

7. A compound of claim 1, (+)-B-iododiiso-2-ethylapopinocampheylborane.

8. A compound of claim 1, (−)-B-fluorodiiso-2-ethylapopinocampheylborane.

9. A compound of claim 1, (+)-B-fluorodiiso-2-ethylapopinocampheylborane.

* * * * *